(12) United States Patent
Chen et al.

(10) Patent No.: US 12,367,589 B2
(45) Date of Patent: Jul. 22, 2025

(54) METHOD AND TERMINAL FOR DETECTING PROTRUSION IN INTESTINAL TRACT, AND COMPUTER-READABLE STORAGE MEDIUM

(71) Applicant: BEIJING GMINE VISION TECHNOLOGIES LTD., Beijing (CN)

(72) Inventors: Wei Chen, Beijing (CN); Boyang Wu, Beijing (CN)

(73) Assignee: BEIJING GMINE VISION TECHNOLOGIES LTD., Beijing (CN)

( * ) Notice: Subject to any disclaimer, the term of this patent is extended or adjusted under 35 U.S.C. 154(b) by 654 days.

(21) Appl. No.: 17/774,204

(22) PCT Filed: Nov. 4, 2020

(86) PCT No.: PCT/CN2020/126488
§ 371 (c)(1),
(2) Date: May 4, 2022

(87) PCT Pub. No.: WO2021/088868
PCT Pub. Date: May 14, 2021

(65) Prior Publication Data
US 2022/0351388 A1    Nov. 3, 2022

(30) Foreign Application Priority Data

Nov. 5, 2019   (CN) .......................... 201911068702.2
Dec. 26, 2019  (CN) .......................... 201911361335.5

(51) Int. Cl.
*G06T 7/12*     (2017.01)
*G01R 33/48*    (2006.01)
(Continued)

(52) U.S. Cl.
CPC ................ *G06T 7/12* (2017.01); *G01R 33/48* (2013.01); *G06T 3/04* (2024.01); *G06T 3/06* (2024.01);
(Continued)

(58) Field of Classification Search
CPC ...................... G06T 19/20; G06T 2207/30028
(Continued)

(56) References Cited

U.S. PATENT DOCUMENTS

2010/0328311 A1    12/2010  Lakshmanan et al.
2016/0350979 A1*   12/2016  Zeng ................. G06T 15/04
2021/0019939 A1     1/2021  Hu et al.

FOREIGN PATENT DOCUMENTS

CN           1781111 A     5/2006
CN         105261052 A     1/2016
(Continued)

OTHER PUBLICATIONS

Office action issued on Aug. 31, 2023 from US Patent Office in a parent U.S. Appl. No. 17/773,918.
(Continued)

*Primary Examiner* — Peter K Huntsinger
(74) *Attorney, Agent, or Firm* — The PL Law Group, PLLC (57) ABSTRACT

A method of detecting a protrusion in an intestinal tract in a computer according to an embodiment of the present disclosure includes acquiring a three-dimensional model of the intestinal tract scanned by a scanning device, the three-dimensional model comprising three-dimensional data of the intestinal tract; mapping, in the computer, the three-dimensional model to a two-dimensional plane in an area-preserving manner; and detecting an area of the protrusion in the two-dimensional plane. The method can replace traditional modes such as enteroscopy, and the protrusion in
(Continued)

acquiring a three-dimensional model of the intestinal tract scanned by a scanning device, the three-dimensional model comprising three-dimensional data of the intestinal tract — S110 mapping, in a computer, the three-dimensional model to a two-dimensional plane in an area-preserving manner — S130 detecting an area of a protrusion in the two-dimensional plane — S140 the intestinal tract is detected in a painless and low-cost mode.

16 Claims, 8 Drawing Sheets

(51) Int. Cl.
| | | |
|---|---|---|
| *G06T 3/04* | (2024.01) | |
| *G06T 3/06* | (2024.01) | |
| *G06T 3/067* | (2024.01) | |
| *G06T 7/11* | (2017.01) | |
| *G06T 7/13* | (2017.01) | |
| *G06T 7/149* | (2017.01) | |
| *G06T 7/521* | (2017.01) | |
| *G06T 7/62* | (2017.01) | |
| *G06T 7/66* | (2017.01) | |
| *G06T 7/70* | (2017.01) | |
| *G06T 17/20* | (2006.01) | |
| *G06T 19/20* | (2011.01) | |
| *G16H 30/20* | (2018.01) | |
| *G16H 30/40* | (2018.01) | |

(52) U.S. Cl.
CPC ............... *G06T 3/067* (2024.01); *G06T 7/11* (2017.01); *G06T 7/13* (2017.01); *G06T 7/149* (2017.01); *G06T 7/521* (2017.01); *G06T 7/62* (2017.01); *G06T 7/66* (2017.01); *G06T 7/70* (2017.01); *G06T 17/20* (2013.01); *G06T 19/20* (2013.01); *G16H 30/20* (2018.01); *G16H 30/40* (2018.01); *G06T 2200/08* (2013.01); *G06T 2207/10024* (2013.01); *G06T 2207/10028* (2013.01); *G06T 2207/10081* (2013.01); *G06T 2207/10088* (2013.01); *G06T 2207/10108* (2013.01); *G06T 2207/20021* (2013.01); *G06T 2207/30016* (2013.01); *G06T 2207/30028* (2013.01); *G06T 2210/41* (2013.01); *G06T 2219/2008* (2013.01); *G06T 2219/2021* (2013.01)

(58) Field of Classification Search
USPC .......................................................... 382/131
See application file for complete search history.

(56) References Cited

FOREIGN PATENT DOCUMENTS

| | | |
|---|---|---|
| CN | 105411505 A | 3/2016 |
| CN | 105741270 A | 7/2016 |
| CN | 107146287 A | 9/2017 |
| CN | 108648231 A | 10/2018 |
| CN | 108875813 A | 11/2018 |
| CN | 110766692 A | 2/2020 |
| CN | 111127314 A | 5/2020 |
| WO | WO 2019/146903 A1 | 8/2019 |

OTHER PUBLICATIONS

Office action issued on Jul. 17, 2023 from US Patent Office in a parent U.S. Appl. No. 17/773,932.

Havaei M, et al., "Within-brain classification for brain tumor segmentation", International journal of computer assisted radiology and surgery. May 2009;11 :777-88, 2016.

Wu Ming-Ni et al., "Brain tumor detection using color-based k-means clustering segmentation", In Third international conference on intelligent information hiding and multimedia signal processing, (IIH-MSP 2007), Nov. 2, 20076 (vol. 2, pp. 245-250). IEEE.

Shen Y et al., "Brain tumor segmentation on MRI with missing modalities", Information processing in Medical imaging: 26th International Conference, IPMI 2019, Hong Kong, China, Jun. 2-7, 2019, Proceedings 26 2019 (pp. 417-428).

Tu Z. et al.,, "Auto-context and its application to high-level vision tasks and 3D brain image segmentation", IEEE transactions on pattern analysis and machine intelligence. Dec. 1, 2009;32(10):17 44-57.

International Search Report for PCT/KR2020/126488 mailed on Feb. 10, 2021.

\* cited by examiner

```
┌─────────────────────────────────────────────────────────┐
│ acquiring a three-dimensional model of the intestinal tract scanned │  S110
│ by a scanning device, the three-dimensional model comprising        │
│        three-dimensional data of the intestinal tract               │
└─────────────────────────────────────────────────────────┘
                              ▼
┌─────────────────────────────────────────────────────────┐  S120
│   performing topology repair on the three-dimensional model        │
└─────────────────────────────────────────────────────────┘
                              ▼
┌─────────────────────────────────────────────────────────┐  S130
│  mapping, in a computer, the three-dimensional model to a two-     │
│        dimensional plane in an area-preserving manner              │
└─────────────────────────────────────────────────────────┘
                              ▼
┌─────────────────────────────────────────────────────────┐  S140
│     detecting an area of a protrusion in the two-dimensional plane │
└─────────────────────────────────────────────────────────┘
```

FIG. 4

```
┌─────────────────────────────────────────────────────────┐  S1201
│   determining positions of genera in the three-dimensional model   │
└─────────────────────────────────────────────────────────┘
                              ▼
┌─────────────────────────────────────────────────────────┐  S1203
│   eliminating the determined genera to reduce the number of the    │
│           genera in the three-dimensional model                    │
└─────────────────────────────────────────────────────────┘
```

```
initializing the second weight of each harmonic mapping point,        S6301
wherein at least three harmonic mapping points form one initial face
                              │
                              ▼
determining weighted dual points of each initial face, the weighted
dual points having equal weighted distances to vertices of each initial   S6303
face, wherein the dual points are connected to form a dual face of the
weighted dual points, and a plurality of dual faces determine a
weighted Voronoi diagram
                              │
                              ▼
updating the second weight of each harmonic mapping point and         S6305
readjusting the weighted Voronoi diagram according to the updated
second weight
```

```
┌─────────────────────────────────────────────────────────────────┐  S6401
│   determining a center of gravity of each dual face in the weighted │
│                        Voronoi diagram                              │
└─────────────────────────────────────────────────────────────────┘
                                    │
                                    ▼
┌─────────────────────────────────────────────────────────────────┐  S6403
│ mapping each of the harmonic mapping points to the center of gravity of │
│   each dual face, thereby mapping the three-dimensional model to the    │
│        two-dimensional plane in the area-preserving manner              │
└─────────────────────────────────────────────────────────────────┘
```

METHOD AND TERMINAL FOR DETECTING PROTRUSION IN INTESTINAL TRACT, AND COMPUTER-READABLE STORAGE MEDIUM

CROSS-REFERENCE TO RELATED APPLICATIONS

This application claims benefit under 35 U.S.C. 119, 120, 121, or 365(c), and is a National Stage entry from International Application No. PCT/CN2020/126488, filed Nov. 4, 2020, which claims priority to the benefit of Chinese Patent Application Nos. 201911068702.2 filed on Nov. 5, 2019 and 201911361335.5 filed on Dec. 26, 2019 in the Chinese Intellectual Property Office, the entire contents of which are incorporated herein by reference.

BACKGROUND

1. Technical Field

This invention relates generally to the field of iconology, and more particularly to the field of medical imaging.

2. Background Art

Clinical applications of medical imaging technology generally refer to researching image formation, retrieval and storage technologies and instrument research and development science. Various imaging devices, such as X-ray, computer aided tomographic (CT), ultrasonic devices, etc., are widely used in a field of biomedical imaging technology.

The wide application of the imaging technology in the medical field is helpful for accurately detecting forms of various tissues or organs in a human body and helps health workers accurately acquire and analyze various data without performing any harmful operation for the human body, so that patient's pain can be greatly relieved, and health and life risks of the patient caused by harmful detection such as the operation and the like are reduced.

An intestinal disease has become a major threat to human health. During detection for the intestinal disease, the detection is usually performed by means of intervention. For example, detection can be performed by enteroscopy to determine whether there is an ulceration or polyp in an intestinal tract, which requires a detection device to be deep into the intestinal tract of the human body, so that great pain will be brought to the patient and it is easy to damage the intestinal tract and even cause unnecessary infection if an operator does not operate properly.

The Chinese patent publication CN105411505 discloses a device and method of controlling movement of a capsule endoscope in a digestive tract of a human body. In that patent, the endoscope is provided in the capsule-like device, the "capsule" is swallowed by a patient and its action is controlled by means of a magnetic field, so that a scene in an intestinal tract and stomach is shot to facilitate a doctor's diagnosis. Compared with the traditional enteroscope detection, the capsule-type endoscope can obviously relieve the patient's pain and reduce damage to intestinal tissue.

However, unlike other organs with smooth inner walls, there are a very large number of folds in the intestinal tract, and some detected parts may be just hidden in these folds. These parts hidden in the folds are very easily overlooked or not detected at all when the enteroscope marches in the intestinal tract. For some minor ulcers or polyps, they are easily missed by the conventional detection measures, so that patient's treatment may be delayed.

It can be seen that, in the prior art, on the one hand, the detection of the intestinal tract needs intervention, which is easy to bring pain and risk to the patient; on the other hand, the hidden diseased part cannot be well detected by the conventional detection method because there are rich folds in the intestinal tract.

SUMMARY

It is an objective of the present disclosure to provide a method capable of accurately detecting a protrusion (such as an intestinal tract polyp) in an intestinal tract in a non-interventional manner.

According to an aspect of the present disclosure, there is provided a method of detecting a protrusion in an intestinal tract, comprising: acquiring a three-dimensional model of the intestinal tract scanned by a scanning device, the three-dimensional model comprising three-dimensional data of the intestinal tract; mapping, in a computer, the three-dimensional model to a two-dimensional plane in an area-preserving manner; and detecting an area of the protrusion in the two-dimensional plane.

According to an embodiment of the present invention, the acquiring a three-dimensional model of the intestinal tract comprises: acquiring a plurality of sections containing intestinal tract information; positioning the intestinal tract information in the plurality of sections; and forming the three-dimensional model from the positioned intestinal tract information.

According to an embodiment of the present invention, wherein the plurality of sections containing the intestinal tract information is acquired by one of: acquiring the plurality of sections by CT scanning technology; acquiring the plurality of sections by a magnetic resonance (MR) device; and acquiring the plurality of sections by single photon emission computed tomography (SPECT).

According to an embodiment of the present invention, the positioning the intestinal tract information in the plurality of sections comprises: positioning the intestinal tract information by edge detection or curvature segmentation.

According to an embodiment of the present invention, the method further comprises: performing topology repair on the formed three-dimensional model.

According to an embodiment of the present invention, the performing topology repair on the formed three-dimensional model comprises: determining positions of genera in the three-dimensional model; eliminating the genera to reduce the number of the genera in the three-dimensional model.

According to an embodiment of the present invention, wherein the mapping the three-dimensional model to a two-dimensional plane in an area-preserving manner comprises: determining a boundary of the two-dimensional plane; harmonically mapping the three-dimensional data to an interior of the boundary to form harmonic mapping points; calculating second weights of the harmonic mapping points, and further calculating a weighted Voronoi diagram of the harmonic mapping points; and mapping the three-dimensional model to the two-dimensional plane in the area-preserving manner according to the weighted Voronoi diagram.

According to an embodiment of the present invention, the boundary of the two-dimensional plane is a rectangle.

According to an embodiment of the present invention, the determining a boundary of the two-dimensional plane comprises: determining a closed curve L in the three-dimensional model; selecting four points $v_0$, $v_1$, $v_2$, $v_3$, from the closed curve L, and letting $\gamma_0=v_0-v_1$, $\gamma_1=v_1-v_2$, $\gamma_2=v_2-v_3$, $\gamma_3=v_3-v_0$; and mapping $\gamma_0\sim\gamma_3$ to four edges of the rectangle, respectively.

According to an embodiment of the present invention, the harmonically mapping the three-dimensional data to an interior of the boundary to form harmonic mapping points comprises: initializing the three-dimensional data to form mapping points in the two-dimensional plane; calculating a harmonic energy between the mapping points in the two-dimensional plane; adjusting the harmonic energy, and stopping the adjustment when the harmonic energy is less than a preset energy gradient threshold; and taking, as the harmonic mapping points, coordinates of the mapping points when the adjustment is stopped.

According to an embodiment of the present invention, wherein the calculating a harmonic energy between the mapping points in the two-dimensional plane comprises: calculating a square value of differences between locations of adjacent mapping points; calculating a first product of the square value and a first weight of an edge formed by the adjacent mapping points; and calculating a sum of the first products for all the mapping points.

According to an embodiment of the present invention, wherein the first weight of the edge formed by the adjacent mapping points is calculated by: determining an angle of a triangle that corresponds to the edge; if the edge is an edge common to two triangles, the first weight of the edge being equal to half of a sum of cotangent trigonometric functions of angles that are opposite to the edge in the two triangles; if the edge is an edge on the boundary, the first weight of the edge being equal to half of a cotangent trigonometric function of an angle that is opposite to the edge in a triangle where the edge is located.

According to an embodiment of the present invention, wherein the calculating second weights of the harmonic mapping points and further calculating a weighted Voronoi diagram of the harmonic mapping points comprises: initializing the second weight of each harmonic mapping point, wherein at least three harmonic mapping points form one initial face; determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and updating the second weight of each harmonic mapping point, and readjusting the weighted Voronoi diagram according to the updated second weight.

According to an embodiment of the present invention, wherein the updating the second weight of each harmonic mapping point comprises: determining an area $A_i$ of an initial face of each harmonic mapping point; determining an area $A_i'$ of a dual face of each harmonic mapping point; determining an area gradient $g_i=A_i-A_i'$ of each harmonic mapping point; determining a sum of squares of the area gradients of all the harmonic mapping points; if the sum of squares is greater than a preset weight threshold, decreasing the second weight until the sum of squares is less than the weight threshold.

According to an embodiment of the present invention, wherein the mapping the three-dimensional model to the two-dimensional plane in the area-preserving manner according to the weighted Voronoi diagram comprises: determining a center of gravity of each dual face in the weighted Voronoi diagram; and mapping each of the harmonic mapping points to the center of gravity of each dual face, thereby mapping the three-dimensional model to the two-dimensional plane in the area-preserving manner.

According to an embodiment of the present invention, detecting the protrusion in the two-dimensional plane comprises: calculating the area of the protrusion.

According to a second aspect of the present invention, there is provided a device for detecting a protrusion in an intestinal tract, comprising: first means configured to acquire a three-dimensional model of the intestinal tract, the three-dimensional model comprising three-dimensional data of the intestinal tract; second means configured to map the three-dimensional model to a two-dimensional plane in an area-preserving manner; and third means configured to detect an area of the protrusion in the two-dimensional plane.

According to a third aspect of the present invention, there is provided a terminal for detecting a protrusion in an intestinal tract, comprising: a processor; a memory connected with the processor, the memory having stored therein computer program code which, when executed, causes the processor to perform the method as described above.

According to a fourth aspect of the present invention, there is provided a computer-readable storage medium having stored thereon computer-readable instructions which, when executed by one or more processors, implement the method as described above.

At least one beneficial effect of the present invention is that the protrusion in the intestinal tract can be accurately judged without intervention and damage to the intestinal tract body, thereby providing powerful support for subsequent work.

BRIEF DESCRIPTION OF THE DRAWINGS

With reference to the accompanying drawings, the above features of the present invention can be better understood and its numerous objectives, features, and advantages are obvious to those skilled in the art, in which identical reference numerals refer to identical elements, and in which.

DETAILED DESCRIPTION

Technical solutions in embodiments of the present invention will be clearly and completely described below with reference to the drawings in the embodiments of the present invention. It is obvious that the embodiments described are only some of the embodiments of the present invention, not all of them. Based on the embodiments in the present invention, all other embodiments, which can be obtained by those skilled in the art without making any creative effort, fall within the protection scope of the present invention.

It should be understood that terms "first", "second", "third", and "fourth", etc. in the claims, description, and drawings of the present disclosure are used for distinguishing different objects, rather than describing a specific order. Terms "comprise" and "include" used in the description and claims of the present disclosure, indicate the presence of stated features, whole, steps, operations, elements, and/or components, but do not preclude the presence or addition of one or more other features, whole, steps, operations, elements, components, and/or combination thereof.

It should also be understood that terms used in the description of the present disclosure herein is for the purpose of describing specific embodiments only, but is not intended to limit the present disclosure. As used in the description and claims of this disclosure, "a", "an" and "the" in the singular form are intended to include the plural form, unless other circumstances are clearly indicated in the context. It should be further understood that a term "and/or" used in the description and claims of this disclosure refers to any and all possible combinations of one or more of associated listed items and comprises these combinations.

As used in the description and claims, a term "if" can be interpreted contextually as "when" or "once" or "in response to determining" or "in response to detecting". Similarly, a phrase "if determining" or "if detecting [a described condition or event]" can be interpreted contextually as meaning "once determining" or "in response to determining" or "once detecting [a described condition or event]" or "in response to detecting [a described condition or event]".

The specific embodiments of the present invention are described in detail below in conjunction with the accompanying drawings.

Figure 1:
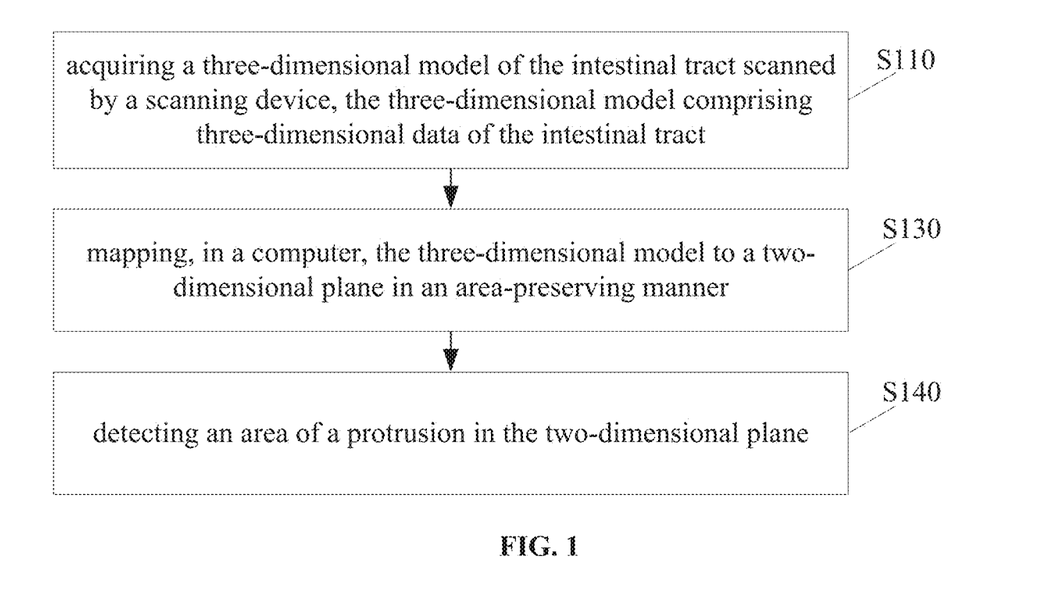
FIG. 1 shows a flow diagram of a method according to an aspect of the present disclosure.

FIG. 1 shows a flow diagram of a method according to an aspect of the present disclosure.

As shown in FIG. 1, the method of the present invention comprises: step S110, acquiring a three-dimensional model of the intestinal tract by means of a scanning device, the three-dimensional model comprising three-dimensional data of the intestinal tract; step S130, mapping, in a computer, the three-dimensional model to a two-dimensional plane in an area-preserving manner; and step S140, detecting an area of a protrusion in the two-dimensional plane.

The intestinal tract is typically an object with rich folds, whose inner surface has a large number of folds that facilitate absorption of nutrients.

It should be understood that the intestinal tract described herein is a physical entity that exists in reality, and the three-dimensional model is a digital representation of the intestinal tract, which can be read, analyzed, processed by the computer, and a desired result can be obtained according to these analysis and processing results.

In addition, in order to accurately detect the protrusion in the intestinal tract and determine a size of the protrusion, performing three-dimensional to two-dimensional mapping in the area-preserving manner is more advantageous than conformal mapping, because the area-preserving mapping has less influence on the area (or a ratio of the area to the total area) of the target object, which is more advantageous for subsequent judgment.

Figure 2:
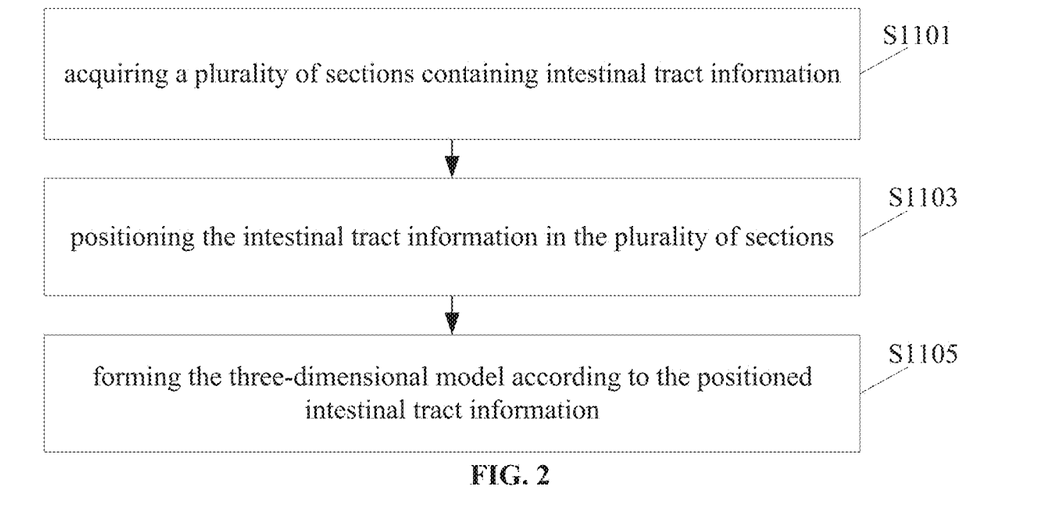
FIG. 2 shows a flow diagram of a method of acquiring a three-dimensional model of an intestinal tract according to an embodiment of the present invention.

FIG. 2 shows a flow diagram of a method of acquiring a three-dimensional model of an intestinal tract according to the present invention.

As shown in FIG. 2, the method comprises: step S1101, acquiring a plurality of sections containing intestinal tract information; step S1103, positioning the intestinal tract information in the plurality of sections; and, step S1105, forming the three-dimensional model according to the positioned intestinal tract information.

The above plurality of sections containing the intestinal tract information can be acquired in various ways.

One way can be to acquire the plurality of sections by CT scanning the intestinal tract; or, to acquire the plurality of sections by a magnetic resonance (MR) device; or, to acquire the plurality of sections by single photon emission computed tomography (SPECT).

Figure 3A:
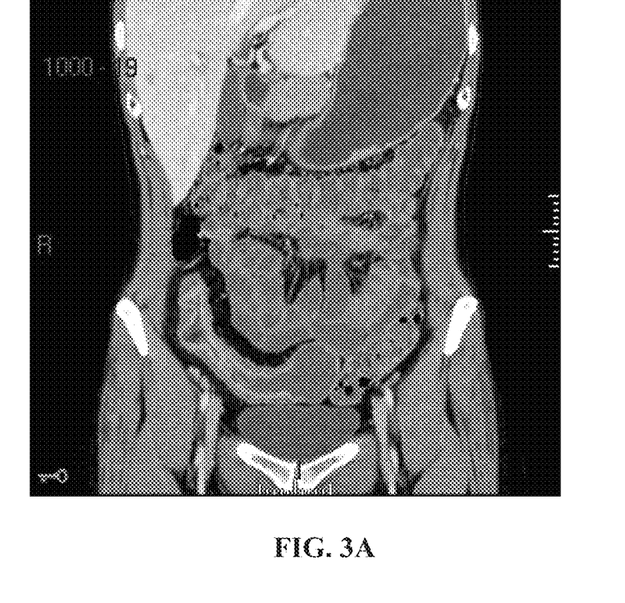
FIG. 3A shows a schematic diagram of a three-dimensional intestinal tract acquired by CT.

FIG. 3A shows a schematic diagram of a three-dimensional intestinal tract acquired by CT.

Taking the CT as an example, generally, if the sections of the intestinal tract are to be acquired, a whole body (especially an abdomen where the intestinal tract is located) of a patient can be scanned, and therefore, the plurality of sections obtained contain information on other organs or parts of the human body, in addition to the information of the intestinal tract. As shown in FIG. 3A, there are other parts of the body in CT scanning images acquired, and therefore the intestinal tract need to be extracted from these images. In other words, it is necessary to position an interested part from the plurality of sections acquired, for example, to position the information of the intestinal tract.

There can be a wide variety of ways to position the information of the intestinal tract. The information of the intestinal tract can be positioned in each section, for example, by edge detection or curvature segmentation for the intestinal tract.

Next, the three-dimensional model of the intestinal tract can be formed from the positioned information of the intestinal tract. According to an embodiment of the present invention, the three-dimensional model of the intestinal tract can be formed by using a classical marching cube algorithm, and the algorithm can be obtained from "Marching cube: a High Resolution 3D Surface Construction Algorithm" of William E. Lorensen and Harvey E. Cline, which will not be described in detail here.

Figure 3B:
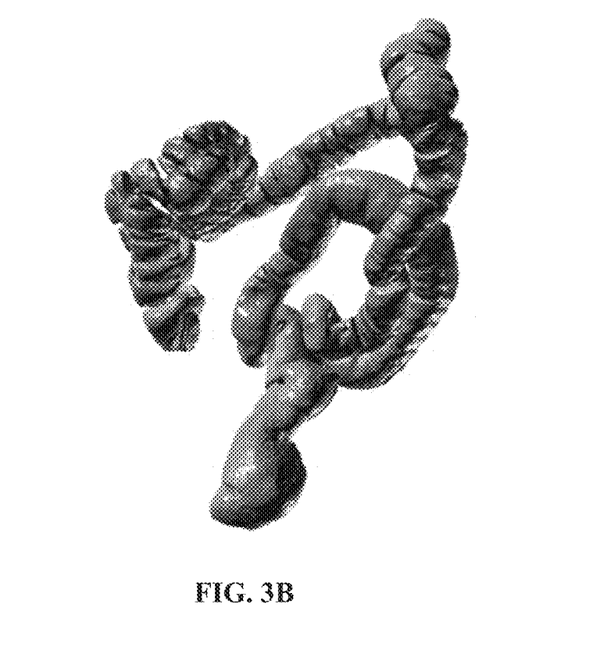
FIG. 3B shows a schematic diagram of an extracted three-dimensional model of a three-dimensional intestinal tract.

In FIG. 3B, a schematic diagram of an extracted three-dimensional model of a three-dimensional intestinal tract is shown.

In general, there will be more noise in the formed three-dimensional model, and the presence of noise will also affect subsequent further mapping.

Figure 4:
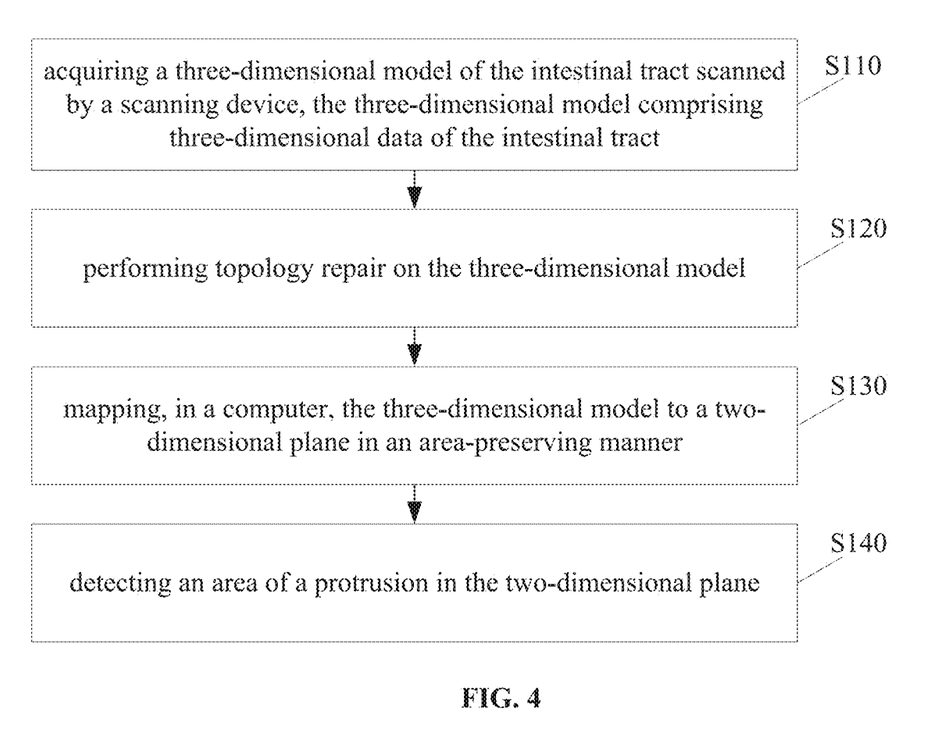
FIG. 4 shows a flow diagram of a method according to an embodiment of the present invention.

According to an embodiment of the present invention, as shown in FIG. 4, the present invention can further comprise, step S120, performing topology repair on the three-dimensional model. The topology repair is geometric shape repair, to repair the imported model into a curved surface with a closed shape, so that the model becomes a whole. Geometry without the topology repair may have face or line missing, or face connection errors.

In the above, for example, we acquire the section images of the intestinal tract through the CT, and obtain dense point cloud on the curved surface of a rectum through image segmentation and contour line extraction, and then obtain the curved surface of the intestinal tract through curved surface reconstruction. After the three-dimensional model is formed, the reconstructed curved surface has many false genera (handles and tunnels) due to image segmentation errors. These false genera need to be detected.

These handles are too tiny to be detected directly by naked eyes. A practical way is to obtain them by methods of calculating topology that usually depend on algorithms of handle loops and tunnel loops of the curved surface. After these false handles are obtained, they are cut along the handle loops, and then gaps are filled to remove topological noise.

Figure 5:
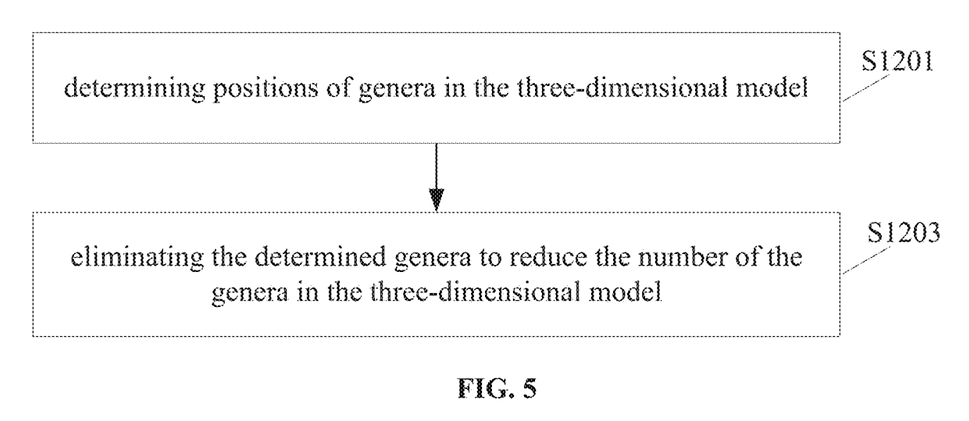
FIG. 5 shows a flow diagram of a method of performing topology repair on a three-dimensional model according to an embodiment of the present invention.

Therefore, according to an embodiment of the present invention, as shown in FIG. 5, the performing topology repair on the formed three-dimensional model comprises: step S1201, determining positions of genera in the three-dimensional model; step S1203, eliminating the determined genera to reduce the number of the genera in the three-dimensional model.

The reducing the number of the genera in the three-dimensional model as described above, preferably, is to reduce the number of the genera to zero, i.e., to implement a zero-genus three-dimensional model, which will help to improve the accuracy of mapping the three-dimensional model to the two-dimensional plane.

The method of mapping the three-dimensional model to a two-dimensional plane in an area-preserving manner is described in detail below.

It should be appreciated that the three-dimensional model is mapped to the two-dimensional plane in many manners. For example, a three-dimensional model can be mapped to a two-dimensional plane in a conformal manner, but this manner has a certain drawback in accurate detection of an area of a protrusion (e.g., intestinal tract polyp), because the conformal manner will cause area information of the three-dimensional object to be lost, so that a size of the protrusion (e.g., intestinal tract polyp) cannot be accurately judged.

In the present invention, however, it is in the area-preserving mapping manner that the three-dimensional object is mapped into the two-dimensional plane, so that areas of all parts in the three-dimensional object are still kept unchanged in the two-dimensional plane, to facilitate subsequent further processing.

Figure 6:
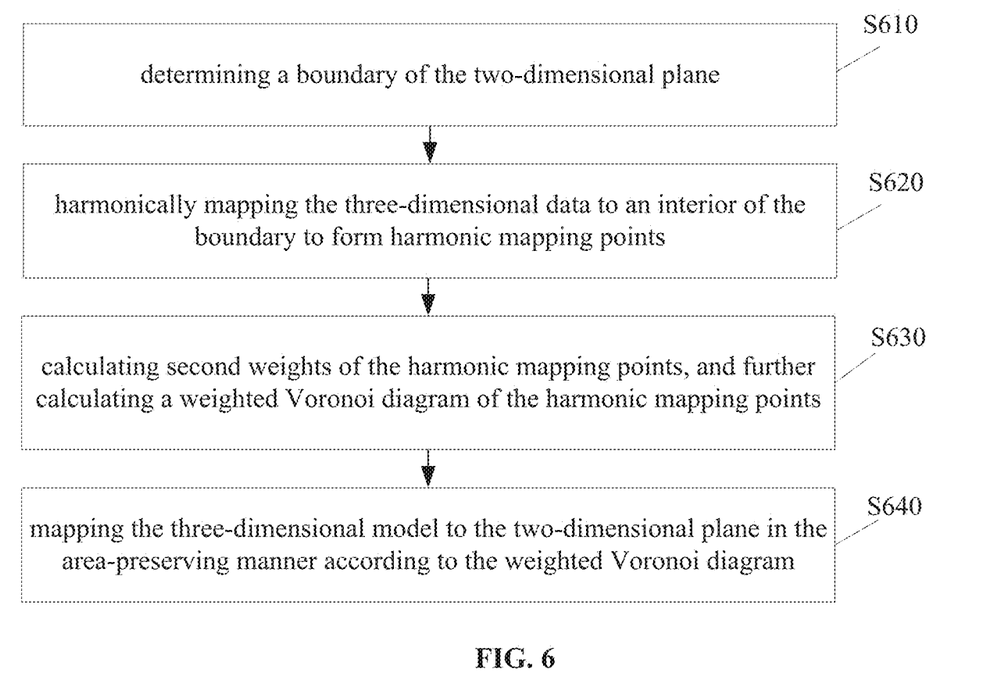
FIG. 6 shows a flow diagram of a method of mapping the three-dimensional model to a two-dimensional plane in an area-preserving manner according to an embodiment of the present invention.

FIG. 6 shows a flow diagram of a method of mapping the three-dimensional model to a two-dimensional plane in an area-preserving manner according to an embodiment of the present invention.

As shown in FIG. 6, the operation of mapping the three-dimensional model to a two-dimensional plane in an area-preserving manner comprises: step S610, determining a boundary of the two-dimensional plane; step S620, harmonically mapping the three-dimensional data to an interior of the boundary to form harmonic mapping points; step S630, calculating second weights of the harmonic mapping points, and further calculating a weighted Voronoi diagram of the harmonic mapping points; step S640, mapping the three-dimensional model to the two-dimensional plane in the area-preserving manner according to the weighted Voronoi diagram.

For the step S610, the boundary of the two-dimensional plane can be determined according to a specific shape of the three-dimensional object. For example, for an intestinal tract, it is similar to a slender object as a whole, and therefore, preferably, the mapped two-dimensional boundary of the intestinal tract can be determined as a rectangle, which will be more conducive to the expansion of the intestinal tract in a mapping process and subsequent reading.

According to an embodiment of the present disclosure, let a closed curve be L, and the boundary of the two-dimensional plane can be established by: selecting four points $v_0$, $v_1$, $v_2$, $v_3$ from the closed curve L, and letting $\gamma_0 = v_0 - v_1$, $\gamma_1 = v_1 - v_2$, $\gamma_2 = v_2 - v_3$, $\gamma_3 = v_3 - v_0$; and mapping $\gamma_0 - \gamma_3$ to four edges of the quadrangle, respectively.

A shape of the quadrangle depends on the selection of edge lengths of the four edges, which are determined according to practical situations.

After the boundary is determined, points in the three-dimensional data that are non-boundary can be mapped to the interior of the two-dimensional plane defined by the boundary. These three-dimensional data can be mapped onto the two-dimensional plane by means of harmonic mapping.

Expressed in a popular way, when the three-dimensional model is mapped to the two-dimensional plane, internal parts of the model can, in themselves, receive certain tensile force due to deformation of the boundary and then spread towards the boundary, and a spreading direction of each point is a result of a resultant force of all points around the point. Until each part no longer changes, it amounts to a "harmonic" state.

Figure 7:
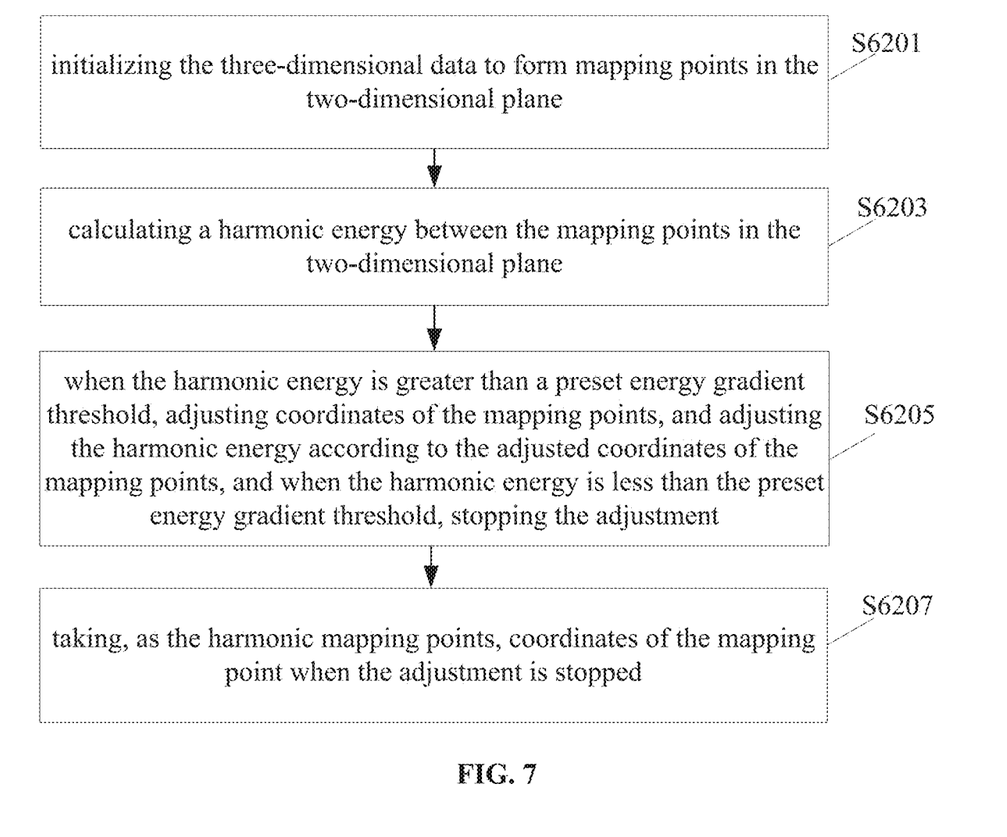
FIG. 7 shows a flow diagram of harmonically mapping three-dimensional data to an interior of a boundary to form harmonic mapping points.

FIG. 7 shows a flow diagram of harmonically mapping three-dimensional data to an interior of a boundary to form harmonic mapping points.

As shown in FIG. 7, therefore, the harmonically mapping the three-dimensional data to an interior of the boundary to form harmonic mapping points comprises: step S6201, initializing the three-dimensional data to form mapping points in the two-dimensional plane; step S6203, calculating a harmonic energy between the mapping points in the two-dimensional plane; step S6205, when the harmonic energy is greater than a preset energy gradient threshold, adjusting coordinates of the mapping points, and adjusting the harmonic energy according to the adjusted coordinates of the mapping points, and when the harmonic energy is less than the preset energy gradient threshold, stopping the adjustment; and, step S6207, taking, as the harmonic mapping points, coordinates of the mapping point when the adjustment is stopped.

The above steps are specifically described below.

For a mesh M, the energy gradient threshold $\delta E$ is preset.

For a non-boundary point, it is initialized to $\vec{f} = (0,0)$, where $\vec{f}$ represents a location of the point in the two-dimensional image. According to an embodiment of the present invention, all three-dimensional data points can be mapped into the two-dimensional plane described above, and initially, all the three-dimensional data points can be mapped to a location (0, 0), which is, of course, only an example, and initially, all the three-dimensional data points can also be mapped into the two-dimensional plane evenly, i.e. all the points are equidistant in the two-dimensional plane.

Next, an initial harmonic energy E is calculated, that is, the harmonic energy between the above mapping points in the two-dimensional plane is calculated. A harmonic energy calculation equation is as follows:

$$E(f)=\Sigma_{[v_i,v_j]\in M}k_{ij}(f(v_j)-f(v_i))^2 \qquad \text{Equation 1}$$

In the above equation, E (f) represents the harmonic energy of all the mapping points, and it can be understood that the initial harmonic energy may be maximum, and thereafter the location of each mapping point will be gradually adjusted so that the harmonic energy gradually decreases and finally falls below the preset energy gradient threshold. At this time, the harmonic state can be reached.

In the above equation, the energy between all the points belonging to the two-dimensional plane (excluding boundary points) and theirs adjacent points is calculated, and according to an embodiment of the present invention, a square value of differences between locations of adjacent mapping points is first calculated; a first product of the square value and a first weight of an edge formed by the adjacent mapping points is calculated; and a sum of the first products for all the mapping points is calculated to obtain the initial harmonic energy.

If the initial harmonic energy is greater than the energy gradient threshold δE, the locations of the corresponding points are adjusted and a new harmonic energy E is recalculated, and the harmonic energy calculated in the previous round is set as $E_0$.

Next, a difference between the new harmonic energy E and the harmonic energy $E_0$ calculated in the previous round is calculated, i.e. whether $|E-E_0|$ is greater than the preset harmonic energy gradient threshold δE. This cycle is continued until the difference between the new harmonic energy E and the harmonic energy $E_0$ calculated in the previous round is not greater than the preset harmonic energy gradient threshold δE. At this time, the energy gradient between all the points is minimum, so that the harmonic state is reached.

The coordinate of each mapping point is calculated by $$\vec{f}(v_i) = \sum_{[v_i,v_j]\in M} \frac{k_{ij}\vec{f}(v_j)}{\sum_j k_{ij}} \qquad \text{Equation 2}$$

where $v_i$ is a representation of the i-th point, $v_j$ is a representation of the j-th point adjacent to i, $f(v_i)$ represents a location of the point $v_i$, and M represents a triangular mesh curved surface, and $k_{ij}$ is a weight of an edge $[v_i, v_j]$.

According to an embodiment of the present disclosure, the first weight of the edge formed by the adjacent mapping points is calculated by: determining an angle of a triangle that corresponds to the edge; if the edge is an edge common to two triangles, the first weight of the edge being equal to half of a sum of cotangent trigonometric functions of angles that are opposite to the edge in the two triangles; and if the edge is an edge on the boundary, the first weight of the edge being equal to half of a cotangent trigonometric function of an angle that is opposite to the edge in a triangle in which the edge is located.

Figure 8:
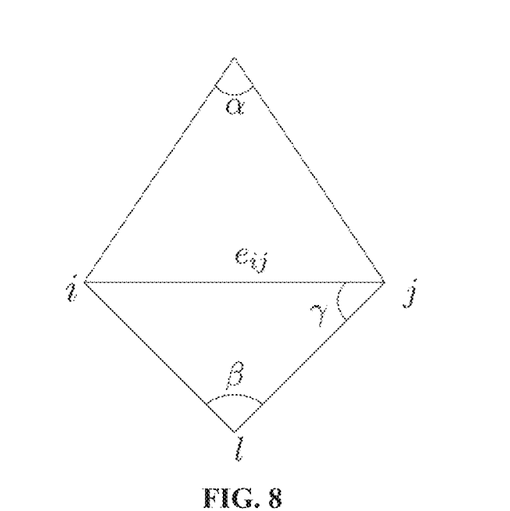
FIG. 8 shows a schematic diagram of calculating a weight of each edge.

For the triangular mesh, there are generally two cases for triangle's edges, wherein one is an edge common to two triangles and the other is an edge of the boundary, as shown in FIG. 8.

In FIG. 8, an edge determined by points i and j is an edge common to two triangles, and an edge determined by points i and l is an edge of the boundary, angles of the two triangles that correspond to the edge $e_{ij}$ are α and β, respectively, and an angle of a triangle that corresponds to the edge $e_{il}$ is γ, and therefore, weights of the two edges are respectively calculated by:

$k_{ij}=\omega(e_{ij})=\frac{1}{2}(\cot \alpha+\cot \beta)$ edge of the interior (having two adjacent faces)

$k_{il}=\omega(e_{il})=\frac{1}{2}\cot \gamma$ edge of the boundary (having only one face)

It can be seen that as locations of the points are continuously adjusted, the angle of each triangle continuously changes, and therefore the weight of the edge also continuously changes. But due to the convergence of this adjustment, the weight of the edge will gradually remain constant, so that the mapping of the image reaches the harmonic state.

In other words, it can be seen from the above description that, as each mapping point is adjusted, the harmonic energy gradually decreases, and eventually reaches less than the specific harmonic energy gradient threshold, thereby realizing the harmonic mapping.

Figure 9:
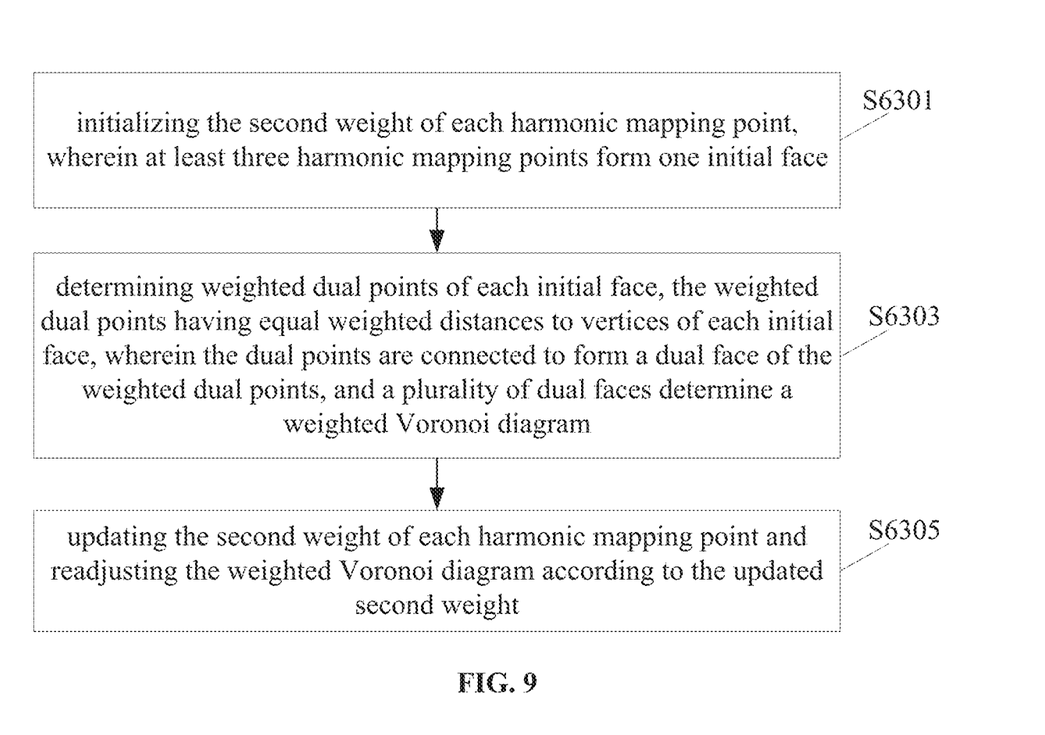
FIG. 9 shows a flow diagram of calculating second weights of harmonic mapping points, and further calculating a weighted Voronoi diagram of the harmonic mapping points according to an embodiment of the present invention.

FIG. 9 shows a flow diagram of calculating second weights of harmonic mapping points and further calculating a weighted Voronoi diagram of the harmonic mapping points according to an embodiment of the present invention.

As shown in FIG. 9, in the present invention, the calculating second weights of the harmonic mapping points and further calculating a weighted Voronoi diagram of the harmonic mapping points comprises:

step S6301, initializing the second weight of each harmonic mapping point, wherein at least three harmonic mapping points form one initial face; step S6303, determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and, step S6305, updating the second weight of each harmonic mapping point and readjusting the weighted Voronoi diagram according to the updated second weight.

Figure 10:
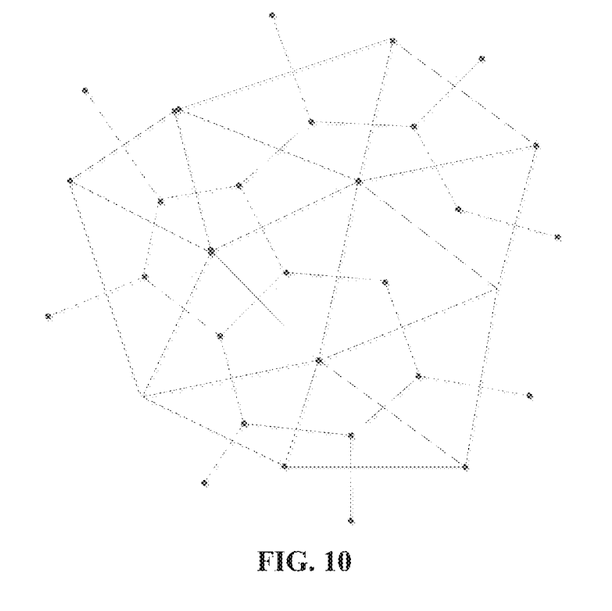
FIG. 10 shows an example of a Voronoi diagram.

First, according to an embodiment of the present invention, the weighted Voronoi diagram is determined on the basis of the formed harmonic mapping points. FIG. 10 shows an example of a Voronoi diagram.

As shown in FIG. 10, the Voronoi diagram is a dual form of the mesh (not limited to a triangular mesh), and taking the triangular mesh as an example, for each face in the mesh, it corresponds to one dual point (vertex of a dotted line) in the Voronoi diagram, the dual point has equal distances to three vertices (i.e., the harmonic mapping points in the above, and vertices of solid lines in FIG. 10), and each point (harmonic mapping point in the present invention) in the original mesh also corresponds to one dual face in the Voronoi diagram, as shown in FIG. 10. However, the weighted Voronoi diagram is different from an ordinary Voronoi diagram in that each point in the original mesh has a weight, and the distance is calculated originally by $d=\|v-q\|^2$, and after the weighting, by $d=\|v-q\|^2+\omega$, so that the adding of the weight ω will make a size of a Voronoi cell change with the weight. The greater weight a vertex of a certain face has, the farther Euclidean distance a circumcenter of the face has to the vertex, so that an area of a dual face corresponding to the vertex will become larger.

The method in FIG. 9 is specifically explained below.

First, a weight of each point is initialized to $\omega_i=0$, and a weight threshold ε is given, for example $\varepsilon=10^{-3}$.

For each face $f_i=[v_a, v_b, v_c]$ in M, its weighted dual point $q_i$ is calculated using the following system of equations, where $v_a$, $v_b$, $v_c$ represent three vertices of each solid-line triangle:

$$\begin{cases} 2(v_a - v_b)^T q_i = \|v_a\|^2 - \|v_b\|^2 + \omega_a - \omega_b \\ 2(v_b - v_c)^T q_i = \|v_b\|^2 - \|v_c\|^2 + \omega_b - \omega_c \end{cases} \quad \text{Equation 3}$$

i.e., $q_i$ has equal weighted distances d to the three points, and $d(q,v)=|v-q|^2+\omega_v$.

$d(q,v)$ is a weighted distance of q and v, and $\omega_v$ is a weight of a point v.

For each solid-line edge in the M, weighted dual points q on both sides of the solid-line edge are connected to form a new dotted-line edge as a dual edge of the solid-line edge.

A new diagram formed by these dual edges is the weighted Voronoi diagram $\Omega$. Each harmonic mapping point, in the weighted Voronoi diagram, corresponds one dual face, which is one cell $Cell_i$, then a current area of each point is $A_i'=area(Cell_i)$.

A gradient $g_i=A_i-A_i'$ of each point is calculated, and let $G=\{g_0, g_1, \ldots, g_n\}$, if $\|G\|^2 < \varepsilon$, iterative updating is stopped, otherwise, let $\omega_i=\omega_i-\lambda g_i$, where $\lambda$ is a step of the gradient descent, needs self-adjustment, and is generally set to be a value less than 1, and a new weight can also be iteratively calculated using a Newton method and the like. $A_i$ is a target area of each harmonic mapping point, i.e., an area in the three-dimensional object that the harmonic mapping point corresponds to.

Figure 11:
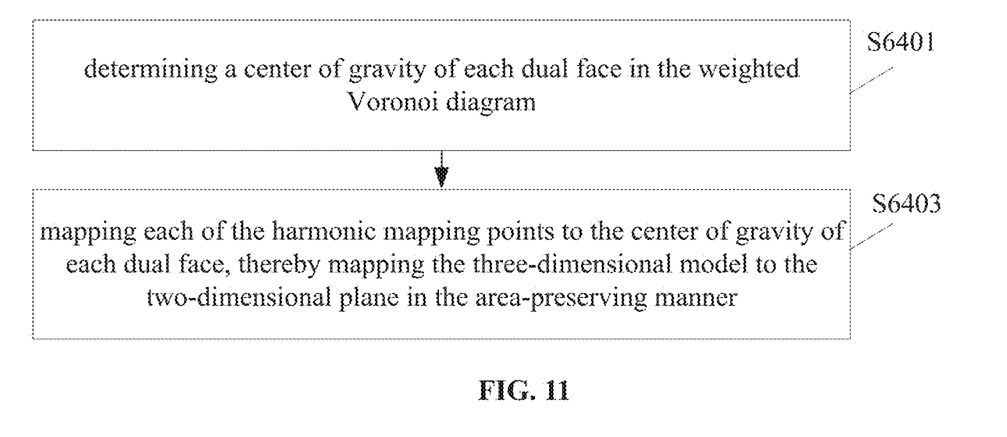
FIG. 11 shows a flow diagram of mapping the three-dimensional model to a two-dimensional plane in an area-preserving manner according to an embodiment of the present invention.

FIG. 11 shows a flow diagram of mapping the three-dimensional model to a two-dimensional plane in an area-preserving manner according to an embodiment of the present invention.

As shown in FIG. 11, the mapping the three-dimensional model to the two-dimensional plane in the area-preserving manner according to the weighted Voronoi diagram comprises: step S6401, determining a center of gravity of each dual face in the weighted Voronoi diagram; step S6403, mapping each of the harmonic mapping points to the center of gravity of each dual face, thereby mapping the three-dimensional model to the two-dimensional plane in the area-preserving manner.

Therefore, by the above method, the three-dimensional data of the intestinal tract can be mapped into the two-dimensional plane in the area-preserving manner.

Figure 13:
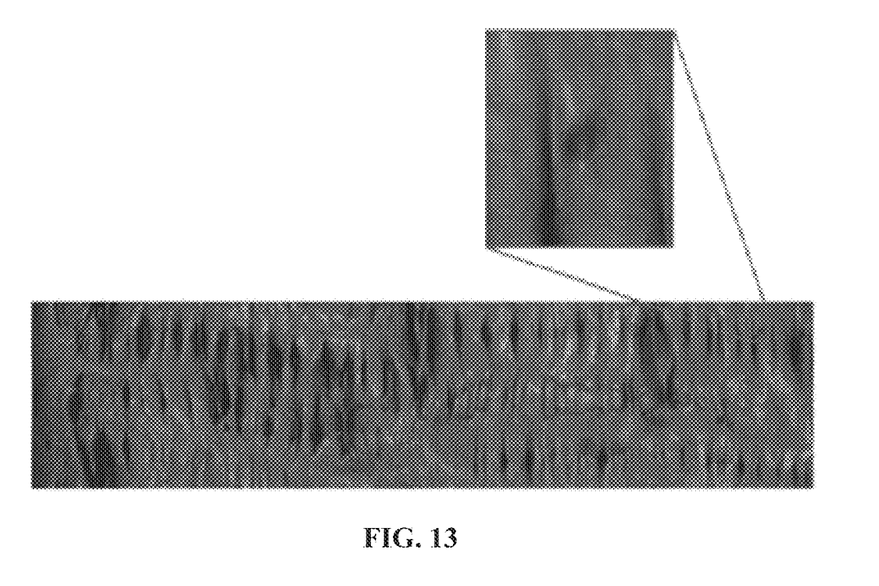
FIG. 13 shows an image of an intestinal tract mapped onto a two-dimensional plane according to an embodiment of the present invention.

FIG. 13 shows an image of an intestinal tract mapped onto a two-dimensional plane according to an embodiment of the present invention.

As shown in FIG. 13, when the three-dimensional data is mapped into the two-dimensional plane, it can be easy to detect a desired region in the plane and check whether there is an abnormality in the region. For example, for an intestinal tract, it can be easy to detect whether there is a polyp in the intestinal tract and determine a size of the polyp. According to the present invention, without the intervention into a human body by using an enteroscope, it can be accurately detected whether there is the polyp in the intestinal tract, thereby helping a doctor give a further suggestion. In addition, in the present invention, the patient has less pain, and detection cost is lower compared with a traditional method.

Figure 12:
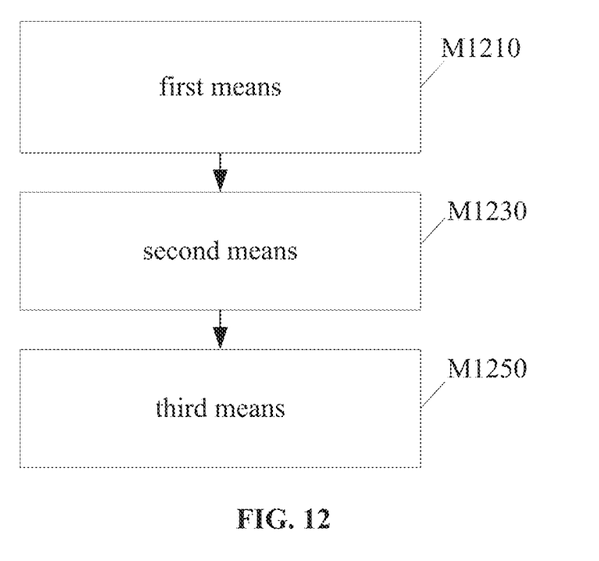
FIG. 12 shows a block diagram of a device according to an aspect of the present invention.

FIG. 12 shows a device for detecting a protrusion in an intestinal tract according to another aspect of the present invention, comprising: first means M1210 configured to acquire a three-dimensional model of the intestinal tract, the three-dimensional model comprising three-dimensional data of the intestinal tract; second means M1230 configured to map the three-dimensional model to a two-dimensional plane in an area-preserving manner; and third means M1250 configured to detect an area of the protrusion in the two-dimensional plane.

The above content can be better understood in light of the following articles:

A1. A method of detecting a protrusion in an intestinal tract, comprising: acquiring a three-dimensional model of the intestinal tract by means of a scanning device, the three-dimensional model comprising three-dimensional data of the intestinal tract; mapping, in a computer, the three-dimensional model to a two-dimensional plane in an area-preserving manner; and detecting an area of the protrusion in the two-dimensional plane.

A2. The method of A1, wherein the acquiring a three-dimensional model of the intestinal tract comprises: acquiring a plurality of sections containing intestinal tract information; positioning the intestinal tract information in the plurality of sections; and forming the three-dimensional model according to the positioned intestinal tract information.

A3. The method of A1 or A2, wherein the plurality of sections containing the intestinal tract information are acquired by one of: acquiring the plurality of sections by CT scanning technology;
acquiring the plurality of sections by a magnetic resonance (MR) device; and acquiring the plurality of sections by single photon emission computed tomography (SPECT).

A4. The method of any of A1 to A3, wherein the positioning the intestinal tract information in the plurality of sections comprises: positioning the intestinal tract information by edge detection or curvature segmentation.

A5. The method of any of A1 to A4, further comprising: performing topology repair on the formed three-dimensional model.

A6. The method of any of A1 to A5, wherein the performing topology repair on the formed three-dimensional model comprises: determining positions of genera in the three-dimensional model; and
eliminating the genera to reduce the number of the genera in the three-dimensional model.

A7. The method of any of A1 to A7, wherein the mapping the three-dimensional model to a two-dimensional plane in an area-preserving manner comprises: determining a boundary of the two-dimensional plane; harmonically mapping the three-dimensional data to an interior of the boundary to form harmonic mapping points; calculating second weights of the harmonic mapping points, and further calculating a weighted Voronoi diagram of the harmonic mapping points; and mapping the three-dimensional model to the two-dimensional plane in the area-preserving manner according to the weighted Voronoi diagram.

A8. The method of any of A1 to A7, wherein the boundary of the two-dimensional plane is a polygon.

A9. The method of any of A1 to A8, wherein the determining a boundary of the two-dimensional plane comprises: determining a closed curve L in the three-dimensional model; selecting four points $v_0$, $v_1$, $v_2$, $v_3$ from the closed curve L, and letting $\gamma_0=v_0-v_1$, $\gamma_1=v_1-v_2$, $\gamma_2=v_2-v_3$, $\gamma_3=v_3-v_0$; and mapping $\gamma_0\sim\gamma_3$ to four edges of the rectangle, respectively.

A10. The method of any of A1 to A9, wherein the harmonically mapping the three-dimensional data to an interior of the boundary to form harmonic mapping points comprises: initializing the three-dimensional data to form mapping points in the two-dimensional plane; calculating a harmonic energy between the mapping points in the two-dimensional plane; when the harmonic energy is greater than a preset energy gradient threshold, adjusting coordinates of the mapping points, and adjusting the harmonic energy according to the adjusted coordinates of the mapping points, and when the harmonic energy is less than the preset energy gradient threshold, stopping the adjustment; and taking, as the harmonic mapping points, coordinates of the mapping points when the adjustment is stopped.

A11. The method of any of A1 to A10, wherein the calculating a harmonic energy between the mapping points in the two-dimensional plane comprises: calculating a square value of differences between locations of adjacent mapping points; calculating a first product of the square value and a first weight of an edge formed by the adjacent mapping points; and calculating a sum of the first products for all the mapping points.

A12. The method of any of A1 to A11, wherein the first weight of the edge formed by the adjacent mapping points is calculated by: determining an angle of a triangle that corresponds to the edge; if the edge is an edge common to two triangles, the first weight of the edge being equal to half of a sum of cotangent trigonometric functions of angles that are opposite to the edge in the two triangles; and if the edge is an edge on the boundary, the first weight of the edge being equal to half of a cotangent trigonometric function of an angle that is opposite to the edge in a triangle where the edge is located.

A13. The method of any of A1 to A12, wherein the calculating second weights of the harmonic mapping points, and further calculating a weighted Voronoi diagram of the harmonic mapping points comprises: initializing the second weight of each harmonic mapping point, wherein at least three harmonic mapping points form one initial face; determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and updating the second weight of each harmonic mapping point, and readjusting the weighted Voronoi diagram according to the updated second weight.

A14. The method of any of A1 to A13, wherein the updating the second weight of each harmonic mapping point comprises: determining an area $A_i$ of an initial face of each harmonic mapping point;

determining an area $A_i'$ of a dual face of each harmonic mapping point; determining an area gradient $g_i = A_i - A_i'$ of each harmonic mapping point; determining a sum of squares of the area gradients of all the harmonic mapping points; and if the sum of squares is greater than a preset weight threshold, reducing the second weight until the sum of squares is less than the weight threshold.

A15. The method of any of A1 to A14, wherein the mapping the three-dimensional model to the two-dimensional plane in the area-preserving manner according to the weighted Voronoi diagram comprises: determining a center of gravity of each dual face in the weighted Voronoi diagram; and mapping each of the harmonic mapping points to the center of gravity of each dual face, thereby mapping the three-dimensional model to the two-dimensional plane in the area-preserving manner.

A16. A terminal for detecting a protrusion in an intestinal tract, comprising: a processor; and a memory connected with the processor, the memory having stored therein computer program code which, when executed, causes the processor to perform the method of any of A1 to A15.

A17. A computer-readable storage medium having stored thereon computer-readable instructions which, when executed by one or more processors, implement the method of any of A1 to A15.

Exemplary Device

It can be appreciated by those skilled in the art that, various aspects of the present invention can be implemented as a system, method or program product. Accordingly, the various aspects of the present invention can be specifically implemented in the following form, an entire hardware embodiment, an entire software embodiment (comprising firmware, microcode, etc.), or an embodiment combining hardware and software aspects, which can be collectively called a "circuit", "module", or "system" herein.

In some possible embodiments, a device for testing an application according to an embodiment of the present invention can comprise at least one processing unit, and at least one storage unit. The storage unit has stored therein program code which, when executed by the processing unit, causes the processing unit to perform the steps in the method of testing the application according to various exemplary embodiments of the present invention as described in the above "exemplary method" section of this specification.

Exemplary Program Product

In some possible embodiments, the various aspects of the present invention can also be implemented in a form of a program product comprising program code which, when the program product is run on the device, causes the device to perform the steps in the method of testing the application according to various exemplary embodiments of the present invention as described in the above "exemplary method" section of this specification.

The program product can employ any combination of one or more readable media. The readable medium can be a readable signal medium or a readable storage medium. The readable storage medium can be, for example, but is not limited to, an electronic, magnetic, optical, electromagnetic, infrared, or semiconductor system, apparatus, or device, or any combination of the above. More specific examples (a non-exhaustive list) of the readable storage medium comprise: an electrical connection having one or more wires, a portable diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the above.

The readable signal medium can comprise a data signal propagated in baseband or as part of a carrier wave, in which readable program code is carried. Such a propagated data signal can take a variety of forms, comprising, but not limited to, an electro-magnetic signal, an optical signal, or any suitable combination of the above. The readable signal medium can also be any readable medium other than the readable storage medium, wherein the readable medium can send, propagate, or transmit a program for use by or in conjunction with an instruction execution system, apparatus, or device.

Program code contained on the readable medium can be transmitted using any appropriate medium, comprising but not limited to wireless, wired, optical cable, RF, etc., or any suitable combination of the above.

Program code for performing operations of the present invention can be written in any combination of one or more programming languages, wherein the programming language comprises an object-oriented programming language such as Java, C++ or the like and also comprises a conventional procedural programming language such as the "C" programming language or a similar programming language. The program code can be executed entirely on a user computing device, partly on the user computing device and partly on a remote computing device, or entirely on the remote computing device or a server. In the case where the remote computing device is involved, the remote computing device can be connected to the user computing device through any kind of network, comprising a local area network (LAN) or a wide area network (WAN), or can be connected to an external computing device (e.g., through the Internet using an internet service provider).

It should be noted that although several units or sub-units of the device are mentioned in the above detailed description, such a division is merely illustrative and not mandatory. In fact, features and functions of two or more units described above can be embodied in one unit according to the embodiments of the present invention. Conversely, features and functions of one unit described above can be further divided and embodied in a plurality of units.

Furthermore, while operations of the methods of the present invention are depicted in the drawings in a specific order, this does not require or imply that these operations must be performed in this specific order, or that all of the illustrated operations must be performed, to achieve desirable results. Additionally or alternatively, certain steps can be omitted, multiple steps can be combined into one step for execution, and/or one step can be broken down into multiple steps for execution.

While the spirit and principles of the present invention have been described with reference to several specific embodiments, it should be understood that the present invention is not limited to the disclosed embodiments, and the division of various aspects does not mean that the features in these aspects cannot be combined to benefit, but is only for the convenience of expression. The present invention is intended to cover various modifications and equivalent arrangements included within the spirit and scope of the attached claims.

What is claimed is:

1. A method of detecting a protrusion in an intestinal tract in a computer, comprising:
    acquiring a three-dimensional model of the intestinal tract scanned by a scanning device, the three-dimensional model comprising three-dimensional data of the intestinal tract;
    mapping, in the computer, the three-dimensional model to a two-dimensional plane in an area-preserving manner; and
    detecting an area of the protrusion in the two-dimensional plane;
    wherein the mapping the three-dimensional model to a two-dimensional plane in an area-preserving manner comprises:
    determining a boundary of the two-dimensional plane;
    harmonically mapping the three-dimensional data to an interior of the boundary to form harmonic mapping points;
    calculating second weights of the harmonic mapping points, and further calculating a weighted Voronoi diagram of the harmonic mapping points; and
    mapping the three-dimensional model to the two-dimensional plane in the area-preserving manner according to the weighted Voronoi diagram.

2. The method of claim 1, wherein the acquiring a three-dimensional model of the intestinal tract comprises:
    acquiring a plurality of sections containing intestinal tract information;
    positioning the intestinal tract information in the plurality of sections; and
    forming the three-dimensional model according to the positioned intestinal tract information.

3. The method of claim 2, wherein the plurality of sections containing the intestinal tract information are acquired by one of:
    acquiring the plurality of sections by CT scanning technology;
    acquiring the plurality of sections by a magnetic resonance (MR) device; and
    acquiring the plurality of sections by single photon emission computed tomography (SPECT).

4. The method of claim 2, wherein the positioning the intestinal tract information in the plurality of sections comprises:
    positioning the intestinal tract information by edge detection or curvature segmentation.

5. The method of claim 2, further comprising:
    performing topology repair on the formed three-dimensional model.

6. The method of claim 5, wherein the performing topology repair on the formed three-dimensional model comprises:
    determining positions of genera in the three-dimensional model; and
    eliminating the genera to reduce the number of the genera in the three-dimensional model.

7. The method of claim 1, wherein the boundary of the two-dimensional plane is a rectangle.

8. The method of claim 7, wherein the determining a boundary of the two-dimensional plane comprises:
    determining a closed curve L in the three-dimensional model;
    selecting four points $v_0, v_1, v_2, v_3$ from the closed curve L, and letting $\gamma_0=v_0-v_1, \gamma_1=v_1-v_2, \gamma_2=v_2-v_3, \gamma_3=v_3-v_0$; and
    mapping $\gamma_0 \sim \gamma_3$ to four edges of the rectangle, respectively.

9. The method of claim 1, wherein the harmonically mapping the three-dimensional data to an interior of the boundary to form harmonic mapping points comprises:
    initializing the three-dimensional data to form mapping points in the two-dimensional plane;
    calculating a harmonic energy between the mapping points in the two-dimensional plane;
    when the harmonic energy is greater than a preset energy gradient threshold, adjusting coordinates of the mapping points, and adjusting the harmonic energy according to the adjusted coordinates of the mapping points, and when the harmonic energy is less than the preset energy gradient threshold, stopping the adjustment; and
    taking, as the harmonic mapping points, coordinates of the mapping points when the adjustment is stopped.

10. The method of claim 9, wherein the calculating a harmonic energy between the mapping points in the two-dimensional plane comprises:
    calculating a square value of a difference between locations of adjacent mapping points;
    calculating a first product of the square value and a first weight of an edge formed by the adjacent mapping points; and
    calculating a sum of the first products for all the mapping points.

11. The method of claim 10, wherein the first weight of the edge formed by the adjacent mapping points is calculated by:
- determining an angle of a triangle that corresponds to the edge;
- if the edge is an edge common to two triangles, the first weight of the edge being equal to half of a sum of cotangent trigonometric functions of angles that are opposite to the edge in the two triangles; and
- if the edge is an edge on the boundary, the first weight of the edge being equal to half of a cotangent trigonometric function of an angle that is opposite to the edge in a triangle where the edge is located.

12. The method of claim 1, wherein the calculating second weights of the harmonic mapping points, and further calculating a weighted Voronoi diagram of the harmonic mapping points comprises:
- initializing the second weight of each harmonic mapping point, wherein at least three harmonic mapping points form one initial face;
- determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and
- updating the second weight of each harmonic mapping point, and readjusting the weighted Voronoi diagram according to the updated second weight.

13. The method of claim 12, wherein the updating the second weight of each harmonic mapping point comprises:
- determining an area $A_i$, of an initial face of each harmonic mapping point;
- determining an area $A_i'$ of a dual face of each harmonic mapping point;
- determining an area gradient $g_i = A_i - A_i'$ of each harmonic mapping point;
- determining a sum of squares of the area gradients of all the harmonic mapping points; and
- if the sum of squares is greater than a preset weight threshold, reducing the second weight until the sum of squares is less than the weight threshold.

14. The method of claim 12, wherein the mapping the three-dimensional model to the two-dimensional plane in the area-preserving manner according to the weighted Voronoi diagram comprises:
- determining a center of gravity of each dual face in the weighted Voronoi diagram; and
- mapping each of the harmonic mapping points to the center of gravity of each dual face, thereby mapping the three-dimensional model to the two-dimensional plane in the area-preserving manner.

15. A terminal for detecting a protrusion in an intestinal tract, comprising:
- a processor; and
- a memory connected with the processor, the memory having stored therein computer program code which, when executed, causes the processor to perform the method of claim 1.

16. A non-transitory computer-readable medium having stored thereon computer-readable instructions which, when executed by one or more processors, implement the method of claim 1.

* * * * *